(12) United States Patent
Lamoncha

(10) Patent No.: US 12,136,488 B2
(45) Date of Patent: *Nov. 5, 2024

(54) PROVIDING GLOBAL ACCESSIBILITY TO PRESCRIBED MEDICATIONS

(71) Applicant: Mark Lamoncha, Columbiana, OH (US)

(72) Inventor: Mark Lamoncha, Columbiana, OH (US)

(*) Notice: Subject to any disclaimer, the term of this patent is extended or adjusted under 35 U.S.C. 154(b) by 574 days.

This patent is subject to a terminal disclaimer.

(21) Appl. No.: 17/388,164

(22) Filed: Jul. 29, 2021

(65) Prior Publication Data

US 2021/0358605 A1 Nov. 18, 2021

Related U.S. Application Data

(63) Continuation-in-part of application No. 17/002,367, filed on Aug. 25, 2020, now Pat. No. 11,386,987, and (Continued)

(51) Int. Cl.
*G16H 40/20* (2018.01)
*G06F 16/2455* (2019.01)
(Continued)

(52) U.S. Cl.
CPC ......... *G16H 40/20* (2018.01); *G06F 16/2455* (2019.01); *G06F 40/263* (2020.01); (Continued)

(58) Field of Classification Search
CPC ........ G16H 10/60; G16H 20/10; G16H 40/20; G16H 70/40; G06Q 20/085; G06Q 30/0185; G06Q 20/381; G06Q 20/389; H04L 63/08
(Continued)

(56) References Cited

U.S. PATENT DOCUMENTS

| | | |
|---|---|---|
| 5,845,255 A | 12/1998 | Mayaud |
| 5,987,519 A | 11/1999 | Peifer et al. |

(Continued)

FOREIGN PATENT DOCUMENTS

| | | | | |
|---|---|---|---|---|
| JP | 2009026344 A | * | 2/2009 | ............ G06F 19/00 |
| WO | 2017139383 A1 | | 8/2017 | |

OTHER PUBLICATIONS

Adeleke, Titus; Blockchain and Learning Organizations: How the Emerging Technology Impacts Knowledge Sharing; University of Maryland University College, ProQuest Dissertations Publishing, 2019. 27672423. (Year: 2019).*

(Continued)

*Primary Examiner* — Hiep V Nguyen
(74) *Attorney, Agent, or Firm* — Standley Law Group LLP; Jeffrey S. Standley; Adam J. Smith

(57) ABSTRACT

Systems and methods for providing world-wide access to prescribed medications are provided. A prescription database receives electronic prescriptions from healthcare provider systems which are stored in one or more blockchains. Each electronic prescription is associated a unique patient identifier in the blockchain(s). Unique patient identifiers are received from pharmacy systems and the electronic prescriptions are retrieved from the patient prescription database for display. Following receipt of dispensation information from the pharmacy systems, new blocks are generated for updating the blockchain(s) at the prescription database.

22 Claims, 12 Drawing Sheets

Related U.S. Application Data a continuation-in-part of application No. 16/550,599, filed on Aug. 26, 2019, now Pat. No. 11,195,605, said application No. 17/002,367 is a continuation-in-part of application No. 16/550,599, filed on Aug. 26, 2019, now Pat. No. 11,195,605.

(51) Int. Cl.

| | | |
|---|---|---|
| *G06F 40/263* | (2020.01) | |
| *G06Q 20/08* | (2012.01) | |
| *G06Q 20/38* | (2012.01) | |
| *G06Q 30/018* | (2023.01) | |
| *G06Q 40/08* | (2012.01) | |
| *G16H 10/60* | (2018.01) | |
| *G16H 20/10* | (2018.01) | |
| *G16H 70/40* | (2018.01) | |
| *H04L 9/40* | (2022.01) | |

(52) U.S. Cl.
CPC ......... *G06Q 20/085* (2013.01); *G06Q 20/381* (2013.01); *G06Q 20/389* (2013.01); *G06Q 30/0185* (2013.01); *G16H 10/60* (2018.01); *G16H 20/10* (2018.01); *G16H 70/40* (2018.01); *H04L 63/08* (2013.01); *G06Q 40/08* (2013.01)

(58) Field of Classification Search
USPC .......................................................... 705/2
See application file for complete search history.

(56) References Cited

U.S. PATENT DOCUMENTS

| 6,523,009 | B1 | 2/2003 | Wilkins |
|---|---|---|---|
| 7,613,620 | B2 | 11/2009 | Salwan |
| 7,769,601 | B1 | 8/2010 | Bleser et al. |
| 8,335,697 | B2 | 12/2012 | Siegel |
| 8,364,504 | B1 | 1/2013 | Bleser et al. |
| 8,510,131 | B1 | 8/2013 | Bleser et al. |
| 2002/0035484 | A1 | 3/2002 | Mccormick |
| 2002/0111829 | A1 | 8/2002 | Robibero |
| 2002/0143434 | A1 | 10/2002 | Greeven et al. |
| 2003/0050802 | A1 | 3/2003 | Jay et al. |
| 2004/0006490 | A1 | 1/2004 | Gingrich et al. |
| 2004/0225527 | A1 | 11/2004 | Holz |
| 2004/0225528 | A1 | 11/2004 | Brock |
| 2005/0182656 | A1 | 8/2005 | Morey |
| 2005/0281601 | A1 | 12/2005 | Papetti |
| 2006/0031094 | A1 | 2/2006 | Cohen et al. |
| 2006/0041330 | A1 | 2/2006 | Ansari et al. |
| 2006/0064326 | A1 | 3/2006 | Tucker |
| 2008/0042423 | A1 | 2/2008 | Roberts et al. |
| 2008/0071572 | A1 | 3/2008 | Ahmed |
| 2009/0106313 | A1 | 4/2009 | Boldyga |
| 2009/0167531 | A1 | 7/2009 | Ferguson |
| 2010/0181374 | A1 | 7/2010 | Martis et al. |
| 2013/0173280 | A1* | 7/2013 | Denny ............... G06Q 20/203 705/2 |
| 2014/0244546 | A1 | 8/2014 | Bezdek et al. |
| 2017/0132393 | A1 | 5/2017 | Natarajan et al. |
| 2017/0147783 | A1* | 5/2017 | Carroll ................ G16Z 99/00 |
| 2019/0198144 | A1* | 6/2019 | Blackley ............. G16H 50/20 |

OTHER PUBLICATIONS

Youdelman, M. et al., Language Services Resource Guide for Pharmacists, Feb. 2010, The National Health Law Program.

Mills et al., Unique health identifiers for universal health coverage, article, published Oct. 17, 2019, 8 pages.

HealthIT.gov, What is Electronic Prescribing?, https://www.healthit.gov/faq/what-electronic-prescribing, site visited Jul. 31, 2020.

American Psychiatric Association, e-Prescribing (eRX), https://www.psychiatry.org/psychiatrists/practice/practice-management/health-information-technology/e-prescribing, site visited Jul. 30, 2020.

Centers for Disease Control and Prevention, Prescription Drug Monitoring Programs (PDMPs), https://www.cdc.gov/drugoverdose/pdmp/states.html, site visited Jul. 30, 2020.

\* cited by examiner

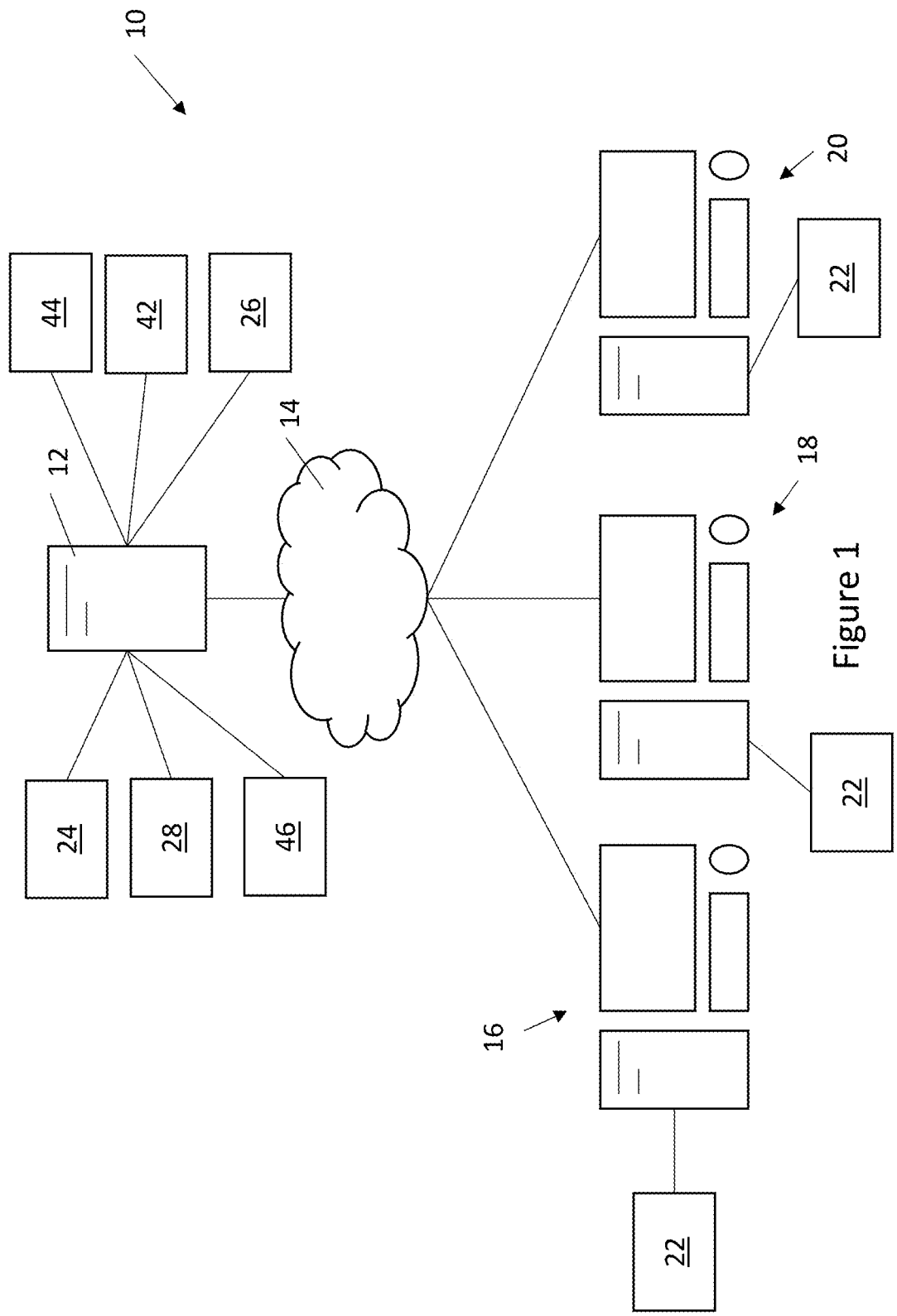

PROVIDING GLOBAL ACCESSIBILITY TO PRESCRIBED MEDICATIONS

CROSS-REFERENCE TO RELATED APPLICATIONS

This application is a continuation in part of U.S. Non-Provisional application Ser. No. 17/002,367 filed Aug. 25, 2020, which is a continuation in part of U.S. Non-Provisional application Ser. No. 16/550,599 filed Aug. 26, 2019 (the "'599 Application"). This application is also a continuation in part of the '599 Application. The disclosures of each of the foregoing are hereby incorporated by reference as if fully restated herein.

TECHNICAL FIELD

Exemplary embodiments relate generally to systems and methods for providing global accessibility to prescribed medications.

BACKGROUND AND SUMMARY OF THE INVENTION

Accessibility to prescribed medications is difficult to obtain when traveling. For example, one might leave for a trip and forget to pack their medication, have their prescription stolen, lose their prescription, or not realize that they only have a two-day supply left in their current prescription, but they are scheduled to be gone for a week. In such cases and others, it may be difficult to obtain needed medications. Even where a prescription is available (new, refill, or the like), it may not be desirable to fully transfer a prescription to another pharmacy. In some cases, the transfer may take several days. For example, transferring pharmacies sometimes have little motivation to move a prescription from their business such that transfers are a low priority item. Indeed, in some cases no refills are even left for a pharmacy to act on. Getting in contact with the prescribing physician to have a new prescription issued at a new pharmacy is time consuming and may then require later transferring the new prescription back to the original pharmacy. This difficulty is sometimes compounded by the fact that access to the medication may be critical to ensuring appropriate care and continued health. As another example, an ongoing global pandemic may leave a patient stranded in a remote location or otherwise render an in-person consultation less than desirable. In such cases, a prescription (new, refill, or the like) may be difficult or impossible to otherwise obtain.

Furthermore, the prescription and dispensation of medication is fraught is fraud. Addicts will stop at little to obtain narcotics or other medications. These addicts will often go so far as to fake symptoms and injuries in the pursuit of drugs. While telemedicine is one way in which patients might remotely consult with a healthcare provider to obtain needed prescriptions, refills, or the like, the remote nature of telehealth consultation brings added risks for fraud. Besides fraud, mistakes and misunderstandings do occur regarding underlying symptoms, conditions, diagnoses, and the like which are used to justify a prescription. Gathering evidence to support prescription of medication may reduce the likelihood of fraud, mistake, and misunderstanding and protect the patient and healthcare provider should such an accusation regarding the same be later made. Therefore, what is needed is a system and method for providing global accessibility to evidence supported, telehealth prescribed medications.

Systems and methods for providing global accessibility to telehealth prescribed medications are disclosed herein. A patient may schedule a consultation with a healthcare provider. The consultation may take place by way of telephonic and/or videographic means, though such is not required. During or following the consultation, the healthcare provider may elect to prescribe one or more medications as part of a new prescription, a refill, or the like. Such prescriptions may be uploaded to a prescription database. In exemplary embodiments, the prescriptions are coupled with evidence of the underlying disease, condition, or injury observed or otherwise collected by the healthcare provider in conjunction with the consultation, though such is not required. For example, without limitation, the evidence may comprise photos of an injury or other condition. Alternatively, or additionally, the evidence may comprise test results, medical imaging results, self-reported symptoms, some combination thereof, or the like. The evidence may be uploaded to the patient prescription database and associated with the prescription.

The prescriptions may reside electronically on the prescription database. The patient prescription database may be the only database that the prescriptions may reside on during their existence, though such is not necessarily required. The patient prescription database may be electronically partitioned so as to provide a private, virtual storage vault for the patient's prescription(s). For example, each of the patient's prescriptions may be contained with a partitioned area of the patient prescription database such that the area is not shared with other patients. The uploaded evidence may be associated with the prescription and be contained within the partitioned area such that the evidence is not shared with other patients, though such is not required. In exemplary embodiments, the prescribing healthcare provider may upload a prescription directly to the patient's partitioned area within the patient prescription database and the prescription may be removed once dispensed or expired. In exemplary embodiments, a unique prescription identifier may be associated with each prescription uploaded to the prescription database.

The evidence may be directly uploaded, though such is not required. In exemplary embodiments, the evidence may remain within the partitioned area or otherwise for a period of time or indefinitely. The evidence may be retrieved when the prescription is accessed to verify the patient's identity. For example, the evidence may show a broken arm and checked against the appearance of the alleged patient for identity verification. Alternatively, or additionally, the evidence may be accessed to compare a patient's current presentation of symptoms, injury, condition, disease, or the like with a former presentation for purposes of evaluating the adequacy of a prescription, the potential for fraud, the need for a refill, the need for further treatment, some combination thereof, or the like. For example, the prescription of a significant amount of powerful narcotic against a relatively minor injury may trigger the dispensing pharmacist to verify the amount, type, or the like of medication prescribed to treat the underlying alleged pain or otherwise flag the prescription as potentially mistaken, fraudulent, or the like.

The patient prescription database may comprise one or more of: a number of prescriptions, a list of unique patient identifiers, a list of unique pharmacist identifiers, and a list of unique healthcare providers. The database may be contained within a single electronic storage device or spread across multiple, locally or remotely located electronic storage devices. Identification information may be stored at the patient prescription database and associated with various patient identifiers. Upon receipt of a patient identifier at a pharmacy system, the patient prescription database may be queried to retrieve information associated with the received unique patient identifier. The information may comprise identification information, prescription information, evidence, some combination thereof, or the like. The information may be sent to the pharmacy system for display.

Alternatively, or additionally, identification information may be entered at the pharmacy system and a match determination may be made against the identification information stored at the patient prescription database for the associated patient identifier. In this way, the identification information may provide a form of authentication. In exemplary embodiments, the identification information may take the form of an identification device, code, password, biometric information, some combination thereof, or the like issued to the patient following enrollment. The identification device may comprise a chip or other storage device comprising the unique patient identifier and various unique prescription identifiers associated with the patient. The identification device may be presented to the pharmacist for reading at the pharmacy system.

Prescriptions associated with the received unique patient identifier may be displayed. One or more of the displayed prescriptions may be selected. Dispensation information, including an amount of medication dispensed, a time and date of dispensation, and a reason for dispensation may be received and updated at the prescription database. The reason for dispensation may be selected from a predetermined list of reasons such as, but not limited to: lost prescription, not enough medication left, theft of medication. Evidence associated with the received unique patient identifier may be displayed. Alternatively, or additionally, the evidence may be retrieved based on its association with retrieved or otherwise accessed prescriptions.

Patients may be provided with read-only access to certain information stored at the patient prescription database associated with an entered unique patient identifier. Such information may include a list of the prescribed medications, evidence, some combination thereof, or the like. Patients may be provided with access by way of a patient system.

Healthcare providers may be provided with write-access to certain information stored at the patient prescription database associated with an entered unique healthcare provider identifier. Healthcare providers may be provided with access by way of a healthcare provider system. Such write-access may be limited to the prescription information and/or evidence, except the dispensation information, which may be provided as read-only or not provided at all.

Pharmacists may be provided with write-access to certain information stored at the patient prescription database associated with an entered unique pharmacist identifier. Pharmacists may be provided with access by way of a pharmacy system. Such write-access may be limited to the dispensation information. Other information, such as a list of prescriptions associated with an entered unique patient identifier and/or evidence, may be provided read-only.

Each unique pharmacist identifier may be associated with a geographic area. Translation of prescription information may be provided based upon the geographic area associated with an entered unique pharmacist identifier. Furthermore, geographic specific brand names and/or generic names may be retrieved for display based upon the geographic area associated with the received pharmacist identifier.

In exemplary embodiments, prescription information from the patient prescription database may only be viewed and/or edited upon successful entry of identifiers from the patient and one or more of: a pharmacist, healthcare provider, and system administrator. In this way, the patient prescription database may require a double verification system. The identifiers may take the form of, for example without limitation, passwords, codes, biometric information, electronic keys, alphanumeric sequences, some combination thereof, or the like. The identifiers may be unique. The identifiers may be of the same or different type for each individual.

In exemplary embodiments, the patient prescription database may be configured to release a copy of, order for, data regarding, some combination thereof, or the like for one or more prescriptions for a given patient based on user provided information. The pharmacy database, and/or related systems, may be configured to display pharmacies geographically proximate a given location and may be further configured to indicate whether the prescribed medication is in stock and/or how long the patient's expected wait time for the prescription may be. Alternatively, or additionally, the patient prescription database and/or related systems may be configured to indicate delivery services available for the given prescribed medications. In exemplary embodiments, only a single fill of a prescription may be released at a given time.

In exemplary embodiments, the patient prescription database and/or related systems may be configured to indicate when the patients' supply of a given medication is expected to be low or out, when a refill is available, some combination thereof, or a like. The patient prescription database or related systems may be configured to notify the patient and/or schedule or provide a listing of available telemedicine appointments.

Blockchains are known, such as for facilitating exchange of cryptocurrencies. A feature of such blockchains generally includes decentralized ledgers. What is needed are systems and methods which utilize such technologies to provide global accessibility to prescribed medications. Systems and methods which utilize blockchain technology to provide global accessibility to prescribed medications are provided. One or more blockchains may be stored at the prescription database. The blockchain(s) may be updated or otherwise managed by a blockchain module. The blockchain(s) may store information regarding prescribed medications. For example, without limitation, such information may include medication(s) prescribed, amount prescribed, number of refills available, number of refills used, refill expiration date, dispensation information, patient information, dispensing pharmacy or pharmacist information, prescriber information, combinations thereof, or the like. The blockchain(s) may be updated, such as by the issuance of new blocks, with each medication prescribed, dispensed, and/or rendered expired by way of non-limiting example. Each newly issued block may comprise a hash of a prior issued block, updates to the prescription information, and a new hash for example, without limitation. Payment for dispensed ones of said prescribed medications may be made by one or more cryptocurrencies.

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 1 is a plan view of an exemplary system;

DETAILED DESCRIPTION OF EXEMPLARY EMBODIMENT(S)

Figure 2A:
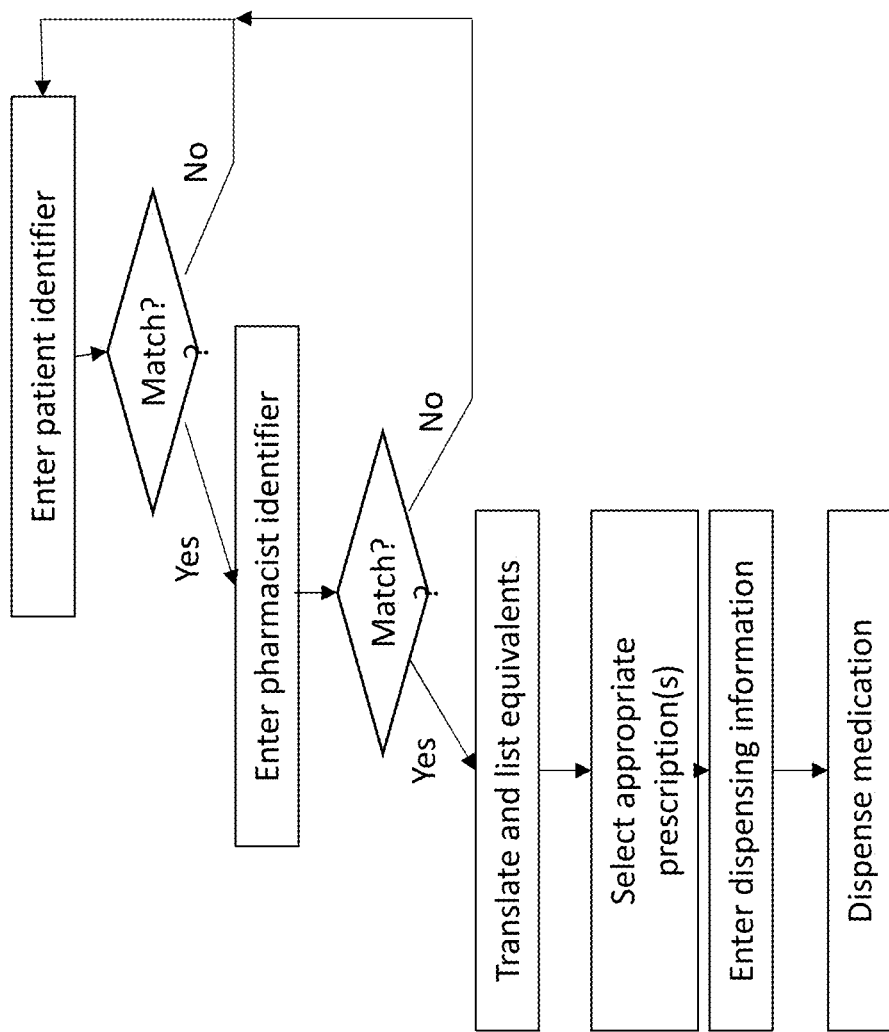
FIG. 2A is a simplified block diagram illustrating exemplary logic for dispensing a prescription using the system.

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

FIG. 1 is a plan view of an exemplary system 10. The system 10 may comprise a patient prescription database 12. The patient prescription database 12 may be in electronic communication with one or more pharmacy systems 16. The patient prescription database 12 may be in electronic communication with one or more patient systems 18. The patient prescription database 12 may be in electronic communication with one or more healthcare provider systems 20. Such electronic communication may be made by way of one or more networks 14.

The patient prescription database 12 may comprise one or more databases, servers, processors, electronic storage devices, some combination thereof, or the like. The patient prescription database 12 may, alternatively or additionally, comprise one or more cloud-based storage systems. The patient prescription database 12 may comprise one or more devices housed at a single location or distributed amongst multiple locations.

Each pharmacy system 16 may be associated with one or more pharmacists, pharmacies, some combination thereof, or the like. Each pharmacy system 16 may comprise one or more electronic devices such as, but not limited to, personal computers, laptops, tablet computers, smartphones, smartwatches, servers, processors, electronic storage devices, some combination thereof, or the like. Each pharmacy system 16 may comprise the same or different components. Each patient system 18 may be associated with one or more patients and may comprise one or more electronic devices such as, but not limited to, personal computers, laptops, tablet computers, smartphones, smartwatches, servers, processors, electronic storage devices, some combination thereof, or the like. Each patient system 18 may comprise the same or different components. Each healthcare provider system 20 may be associated with one or more healthcare providers, offices, some combination thereof, or the like. Each healthcare provider system 20 may comprise one or more electronic devices such as, but not limited to, personal computers, laptops, tablet computers, smartphones, smartwatches, servers, processors, electronic storage devices, some combination thereof, or the like. Each healthcare provider system 20 may comprise the same or different components. The network(s) 14 may comprise one or more internets, intranets, the world wide web, cellular networks, wired networks, wireless networks, LANs, some combination thereof, or the like.

FIG. 2A is a simplified block diagram illustrating exemplary logic for dispensing a prescription using the system 10. An individual may have one or more prescriptions stored at the patient prescription database 12. In exemplary embodiments, the prescriptions are stored in electronic form. Such electronic prescriptions may include scanned or other images of handwritten prescriptions, but preferably include e-prescription documents, data, or information. By way of illustration, without limitation, the individual may have packed for a seven-day cruise only to realize that he or she only has two days' worth of their important heart medication left. The individual may visit the ship's pharmacy to have additional medication dispensed using the system 10. Before dispensing the prescription, the identity of the individual may first be verified.

The individual may identify himself or herself to the pharmacist or other pharmacy team member. The individual may provide a unique patient identifier for the pharmacy team member to enter into the pharmacy system 16, though such is not required. In other exemplary embodiments, the individual may provide the unique patient identifier at the patient system 18.

Alternatively, or additionally, the individual may provide one or more forms of identification to verify that they are who they say they are. Such identification may comprise, for example without limitation, a photo identification, a government issued driving license, a government issued passport, a credit card, a utility bill, some combination thereof, or the like. Such information may be provided manually, or electronically, such as by upload to the pharmacy system 16 and/or the patient system 18. In exemplary embodiments, the pharmacy team member may enter the information at the pharmacy system 16. The information may be entered manually at the pharmacy or patient systems 16, 18, or by way of one or more peripheral devices 22. The peripheral devices 22 may include, for example without limitation, magnetic strip readers, chip readers, imaging devices, cameras, scanners, RFID devices, QR readers, barcode scanners, fingerprint readers, biometric information gathering devices, some combination thereof, or the like. In exemplary embodiments, the presented forms of identification may be stored at the patient prescription database 12 in conjunction with the transaction for later review.

The entered information may be compared with identification information stored at the patient prescription database 12 to determine if the entered information matches the information stored at the patient prescription database 12. In exemplary embodiments, the patient prescription database 12 may be configured to compare an entered unique patient identifier against patient identifiers stored at the patient prescription database 12. Alternatively, or additionally, the patient prescription database 12 may be configured to compare other entered identification information against stored identification information associated with a provided unique patient identifier. In other exemplary embodiments, the entered identification information may be compared against all stored identification information to determine the presence or non-presence of a match.

The match determination may be performed electronically at the patient prescription database 12, though it is contemplated that such matching may instead be performed at the pharmacy system 16 and/or the patient system 18. For example, without limitation, a magnetic strip associated with the driver's license may be read and electronically compared for stored information at the patient prescription database 12.

If no matching information is found, such information may be displayed at the pharmacy system 16 and/or the patient system 18. If a match is found, such information may be displayed at the pharmacy system 16 and/or the patient system 18. Where a match is found, additional features or information may be accessed and/or further steps permitted as shown and described herein. Where no match is found, access to such additional features or information and/or further steps may be denied.

In other exemplary embodiments, stored identification information associated with an entered unique patient identifier may be electronically transmitted from the patient prescription database 12 to the pharmacy system 16 for manual review by the pharmacy team member against the provided identification. Such stored identification information may comprise, for example without limitation, images of various forms of identification, biometric data, patient images, some combination thereof, or the like.

The identification of the dispensing pharmacist and/or pharmacy may be verified. The pharmacy team member may enter a unique pharmacist identifier at the pharmacy system 16. This unique pharmacist identifier may only be provided to pharmacy team members acting under a verified pharmacy license as further described herein. The entered unique pharmacist identifier may be evaluated against unique pharmacist identifiers stored at the patient prescription database patient prescription database 12 to determine if a match exists. The presence or non-presence of a match may be displayed at the pharmacy system 16. Where a match is found, additional features or information may be accessed and/or further steps permitted as shown and described herein. Where no match is found, access to such additional features or information and/or further steps may be denied. In this way, both the patient's identification and the dispensing pharmacy's and/or pharmacist's identification may be verified prior to access to prescription information stored at the patient prescription database 12.

Alternatively, or additionally, identification of the prescribing healthcare provider and/or office may be verified. The healthcare provider team member may enter a unique healthcare provider identifier at the healthcare system 20. This unique healthcare provider identifier may only be provided to healthcare provider team members acting under a verified healthcare provider license as further described herein. The entered unique healthcare provider identifier may be evaluated against unique healthcare provider identifiers stored at the patient prescription database 12 to determine if a match exists. The presence or non-presence of a match may be displayed at the healthcare provider system 20. Where a match is found, additional features or information may be accessed and/or further steps permitted as shown and described herein. Where no match is found, access to such additional features or information and/or further steps may be denied. In this way, both the patient's identification and the prescribing healthcare provider's and/or office's identification may be verified prior to access to prescription information stored at the patient prescription database 12.

A similar technique may be used to verify the identification of one or more system administrators.

In exemplary embodiments, prescription information from the patient prescription database 12 may only be viewed and/or edited upon successful entry of identifiers from the patient and one or more of: a pharmacist, healthcare provider, and system administrator. Such identifiers may be provided by way of respective systems 16, 18, and/or 20. In this way, the patient prescription database may require a double verification system. The identifiers may take the form of, for example without limitation, passwords, codes, biometric information, electronic keys, alphanumeric sequences, some combination thereof, or the like. The identifiers may be uniquely assigned and maintained. The identifiers may be of the same or different type for each individual or entity.

Upon a successful double verification, access to the individual's available prescriptions as listed in the patient prescription database 12 may be generated for display at one or more relevant systems 16, 18, and/or 20. All prescriptions available may be displayed. Expiring prescriptions may be automatically deleted from the patient prescription database 12. Furthermore, prescriptions and accounts associated with one or more individuals, medical care professionals, pharmacy team members, or other users who have not paid a service fee may be automatically deleted. The patient prescription database 12 may be configured to attend to such management efforts automatically. Alternatively, or additionally, one or more administrators may be granted write-access to make such changes manually.

In exemplary embodiments, without limitation, the unique pharmacist identifier may be associated with one or more languages. The prescription information may be automatically translated, by way of a human or machine translation, into the associated language. Such translation may be performed by way of a translation module 24 in electronic communication with the patient prescription database 12. In other exemplary embodiments, the translations may automatically be performed when the prescription entry is created within the system 10, and the appropriate translation may be retrieved and displayed.

The unique pharmacist identifier may be associated with one or more geographic areas. The patient prescription database 12 may be configured to associate each prescription with various equivalents, alternatives, generics, and the like for each geographic area. For example, without limitation, a prescription for a brand name drug may be written and initially dispensed from a pharmacy associated with the United States under the brand name marketed in the United States. However, Europe may have access to different equivalent or alternative drugs than the United States. Alternatively, or additionally, Europe may have the same drug marketed under a different brand or generic name. The patient prescription database 12 may be configured to automatically retrieve the brand name equivalent, alternatives, or generics available in the geographic area associated with the unique pharmacist identification code, which may or may not be available in all geographic areas. In exemplary embodiments, such language and/or geographic areas association maybe automatically determined, or verified, by the IP address of the pharmacy system 16.

Dispensing information for each prescription may be entered at the pharmacy system 16. Such dispensing information may include the identity of medications dispensed, time and date of dispensation, how many units of medication were dispensed (e.g., number of tablets, number of milliliters, etc.), some combination thereof, or the like. Such dispensing information may, alternatively or additionally, comprise a reason for dispensing, which may be a mandatory entry. The reason may be selected from a predetermined list of reasons such as, but not limited to: lost prescription, not enough medication left, or theft of medication. The patient prescription database 12 may be configured to automatically update appropriate prescriptions saved at the database 12 in accordance with such received information.

The patient prescription database 12 may be configured to automatically flag users as potentially fraudulent who request dispensation a certain number of times within a certain time period and/or a particular reason for dispensation with a frequency above a predetermined threshold. So flagged users may be required to provide additional documentation such as, but not limited to, an affidavit, police report, statement from healthcare provider, some combination thereof, or the like. In other exemplary embodiments, some flagged users may have their related prescriptions, or all prescriptions, deleted from the patient prescription database 12, or may be otherwise prevented from obtaining additional medications using the system 10. In exemplary embodiment, the dispensation of each medication may be recorded by way of one or more electronic receipts stored at the patient prescription database 12.

In exemplary embodiments, only a portion of the prescribed medication may be dispensed. For example, just enough to get the user through their immediate needs until they can return to their regular pharmacy may be provided. If a user is traveling on a seven-day cruise and only has two days' worth of medication, for example without limitation, only five days' worth of medication may be dispensed. The pharmacy team member may be required to enter such information as part of the dispensing information. For example, without limitation, the pharmacy team member may be required to provide a detailed explanation for the number of units of medication dispensed for storage at the patient prescription database 12. The explanation may be associated with the dispensation. In this way, the individual's story may be subsequently verified by travel documents, credit card purchases, receipts, passport entries, some combination thereof, or the like.

The amount of medication dispensed, whether a full or partial refill, or the like, may be noted at the patient prescription database 12 and effectively subtracted from remaining available refills, amount of medication, or the like in some cases, such as where the patient indicates they ran out of medication. In other cases, the amount of medication dispensed may not be so subtracted, such as where the patient indicates that the medication was lost or stolen.

Any examples or scenario shown and/or described herein are merely exemplary and are not intended to be limiting. The system and methods described herein may be utilized to fill any number and type of prescriptions such as entire prescription's, new prescriptions, refills, some combination thereof, or the like. In exemplary embodiments, certain medications, or classes of medications, such as but not limited to narcotics, may be restricted from partial fulfilment by the patient prescription database 12. Such restrictions may be geographic specific.

In exemplary embodiments, the patient prescription database 12 may be in electronic communication with a telehealth module 42. The telehealth module 42 may be configured to facilitate telemedicine visits between a patient and the healthcare provider. Such telemedicine visits may include telephonic calls, VOIP calls, video conferencing sessions, text-based exchanges, some combination thereof, or the like. In exemplary embodiments, a patient may elect to participate in a telehealth visit by way of their patient system 18 and/or such a telehealth visit may be required prior to filling or re-filling the prescription in question. Upon receipt of such a request, the telehealth module 42 may be configured to automatically distribute a text message, email, scripted phone call, or other electronic notification to a number of enrolled healthcare providers, by way of the respective healthcare provider systems 20. A healthcare provider may accept the telemedicine request. After the telemedicine experience has been completed, the patient prescription database 12 may be configured to distribute payment to the healthcare providers. The amount disbursed may be automatically billed to the patient and/or his/her insurance provider. The telehealth module 42 may alternatively, or additionally, be configured to facilitate in person visits, such as but not limited to, by coordinating a time, place, and healthcare provider for the visit.

Figure 8:
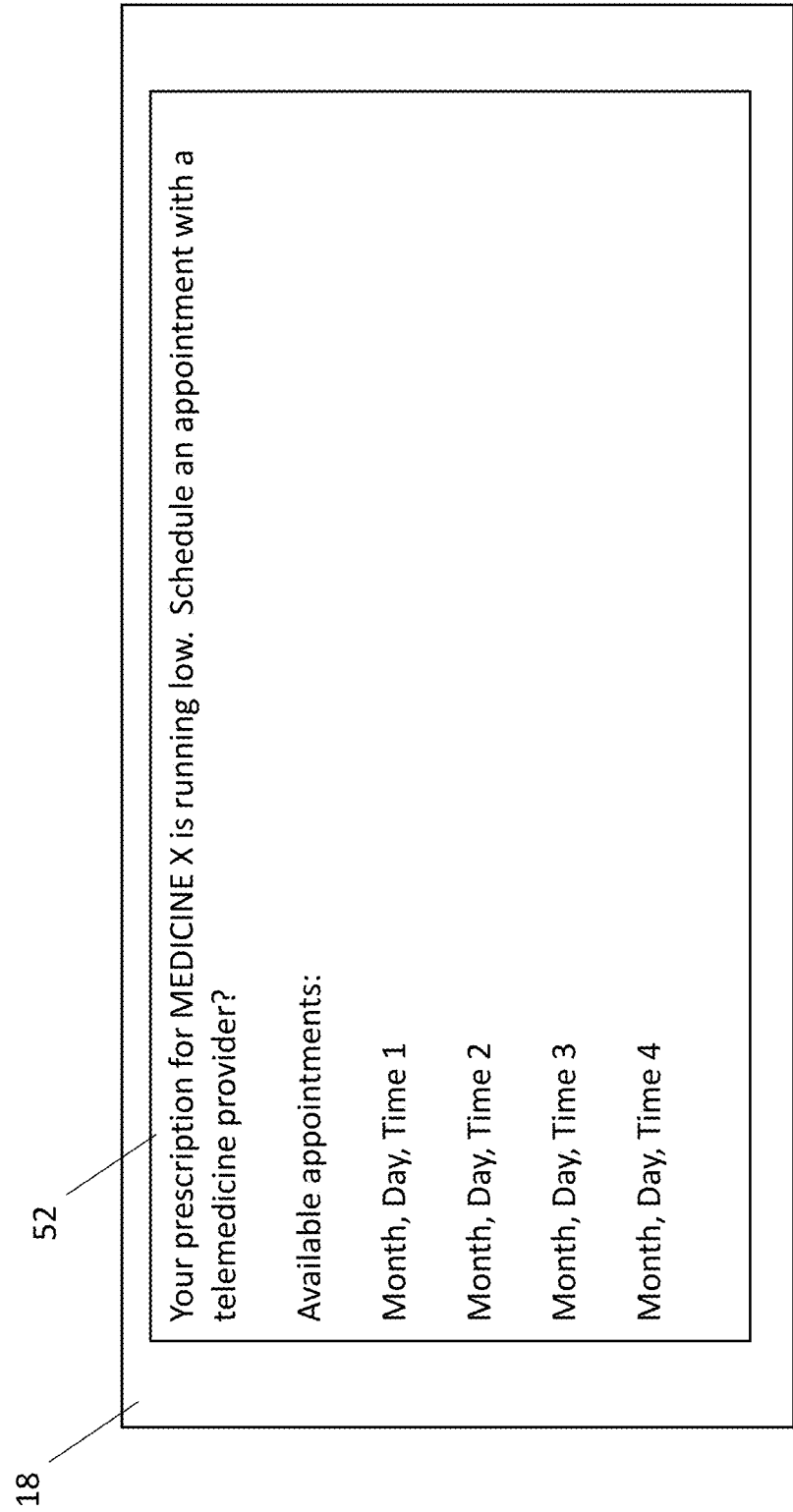
FIG. 8 is a plan view of an exemplary appointment scheduling interface for use with the systems and methods of FIGS. 1-7.

An exemplary user interface 52 at an exemplary patient system 18 is shown at FIG. 8. An electronic notification may be automatically generated and displayed at the patient system 18 by the patient prescription database 12 and/or the telehealth module 42 as prescriptions run low, become expired, or the like. The notification may comprise a prompt for scheduling telemedicine providers. The prompt may comprise a listing of available or descried appointments, such as various dates and times. In other exemplary embodiments, the system may be configured to match patients with available, nearby healthcare providers for an in-person visit.

The patient prescription database 12 may be in electronic communication with an on-call pharmacist module 44. The on-call pharmacist module 44 may be configured to automatically distribute a text message, email, scripted phone call, or other electronic notification to a number of enrolled pharmacists by way of the pharmacy systems 16. A patient may request an on-call pharmacist by way of the patient system 18. The on-call pharmacist module 44 may be configured to match patients with on-call pharmacists located nearby to dispense a prescription. A pharmacist may accept the on-call request. After the prescription is filled, the patient prescription database 12 may be configured to distribute payment to the pharmacist. The amount disbursed may be automatically billed to the patient and/or his/her insurance provider.

The payments and billing discussed herein may be accomplished by way of a billing module 46 in electronic communication with the patient prescription database 12, though such is not required. The billing module 46 may be configured to automatically generate and transmit requests for reimbursement to insurance providers, generate and transmit invoices to the patient, electronically disburse payments to providers, some combination thereof, or the like.

Figure 3:
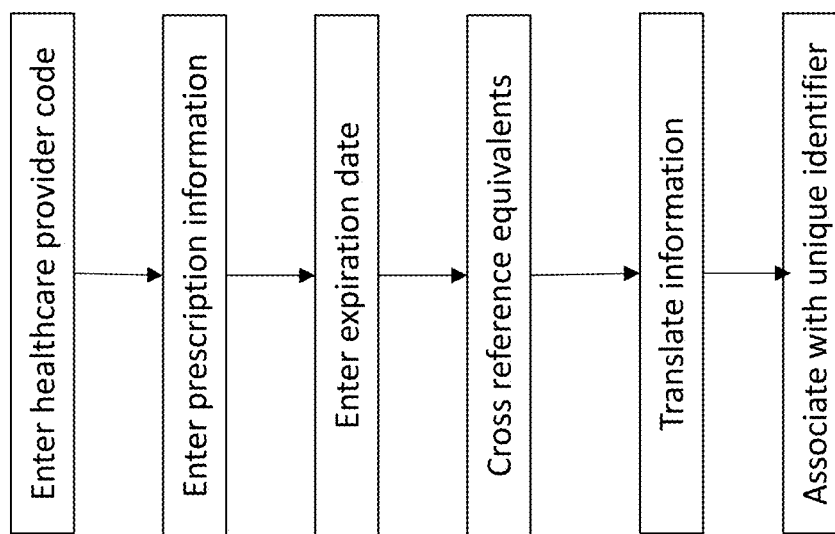
FIG. 3 is a simplified block diagram illustrating exemplary logic for entering a new prescription into the system.

FIG. 3 is a simplified block diagram illustrating exemplary logic for entering a new prescription into the system 10. A healthcare provider may initiate a new prescription within the patient prescription database 12 at a healthcare provider system 20. The healthcare provider may enter a unique healthcare provider identifier. The healthcare provider may enter prescription information. Such prescription information may include, for example without limitation, the name of the medication, the dosage schedule, the amount of medication to be provided, the number of refills available, some combination thereof and the like. In exemplary embodiments, the prescription information may further comprise an expiration date for each prescription. If such information is not provided, the patient prescription database 12 may automatically enter such expiration information. The expiration information may be automatically determined based on the classification of the drug prescribed. Table 1 provides an exemplary list, without limitation, of default expiration time tables for classes of drugs.

TABLE 1

| Class of Drug | Default Expiration |
| --- | --- |
| Narcotic | 1 month |
| Antibiotic | 6 weeks |
| Mood-altering drug | 2 months |
| Over the counter | 1 year |

Table 1 is provided as an example, without limitation. Any default expiration time for any type or class of drug is contemplated. The default expiration may be specific to the geographic region associated with the prescribing healthcare provider and/or the disbursing pharmacy. In exemplary embodiments, the patient prescription database 12 may be configured to automatically set the geographically relevant expiration data based on the location of the prescribing healthcare provider and/or the disbursing pharmacy.

Upon expiration, the prescription may be automatically removed from the patient prescription database 12. The patient prescription database 12 may be configured to find equivalent name brand and/or generic drugs associated with a prescribed medication for each geographic area based on information stored at the patient prescription database 12 or elsewhere. The patient prescription database 12 may be configured to automatically translate the prescription information into a number of languages by way of a human or machine translator, such as by way of the translation module 24.

In exemplary embodiments, a unique prescription identifier may be associated with each prescription uploaded to or otherwise stored at the patient prescription database 12. The unique identifiers described herein may be generated and assigned by a unique identifier module 28 which may be configured to create such unique identifiers. The unique identifier module 28 may be in electronic communication with the patient prescription database 12.

Each unique prescription identifier may be stored at the patient prescription database 12 in a list. Each unique prescription identifier may be associated with one or more unique patient identifiers associated with the patient for whom the prescription is written. Each unique prescription identifier may be associated with one or more unique healthcare provider identifiers associated with the prescribing healthcare provider. The unique prescription identifier may be entered, for example without limitation, by way of one or more of the pharmacy systems 16, the healthcare provider systems 20, and/or the patient systems 18 and the appropriate prescription information may be returned.

Figure 2B:
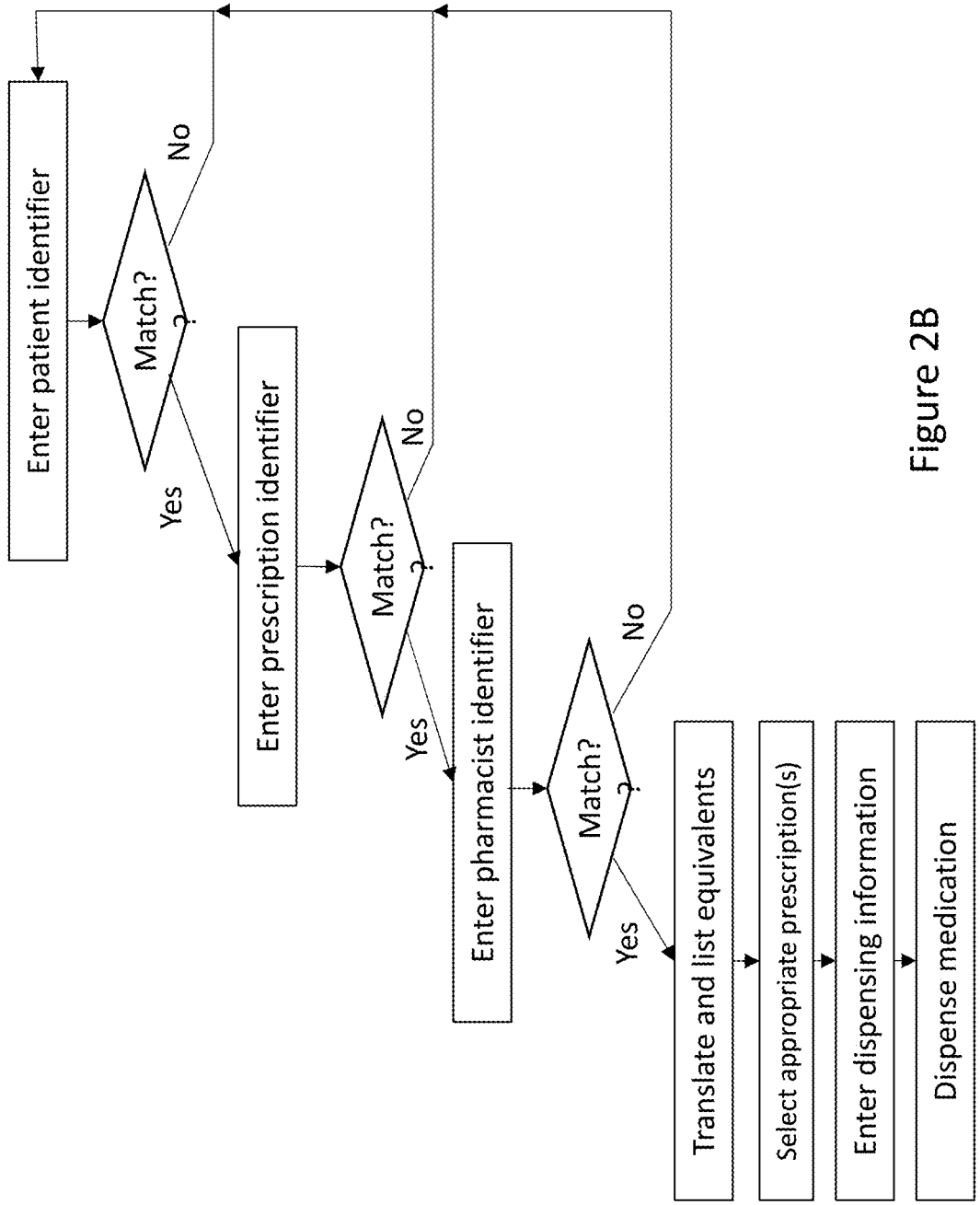
FIG. 2B is a simplified block diagram illustrating other exemplary logic for dispensing a prescription using the system.

As shown in FIG. 2B, a prompt to enter the unique prescription identifier may be generated. Upon entry, a determination may be made as to whether the entered unique prescription identifier matches one of the unique prescription identifiers stored at the patient prescription database 12. This may provide an additional layer of verification. First, the entered unique prescription identifier must match one stored at the patient prescription database 12. Second, the unique patient identifier associated with the matched unique prescription identifier as stored at the patient prescription database 12 may be retrieved and compared to the entered patient identifier to determine a match.

Figure 4:
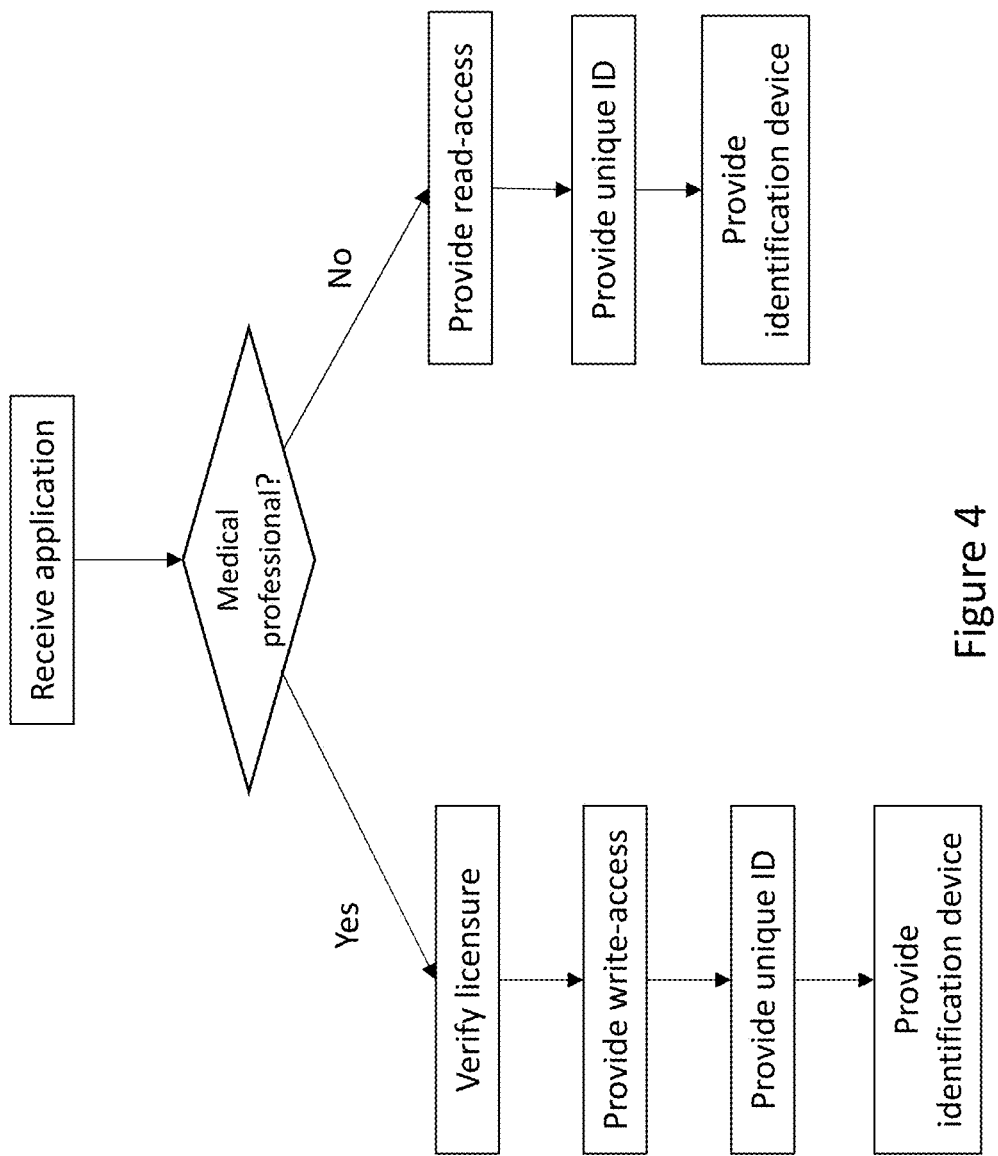
FIG. 4 is a simplified block diagram illustrating exemplary logic for adding a new user to the system.

FIG. 4 is a simplified block diagram illustrating exemplary logic for adding a new user to the system 10. An application for a new user may be received. The application may indicate whether the user is a patient, pharmacist, healthcare provider, or administrator. Each user may be tied to a unique identifier. The unique identifiers may be segregated by type: patient, pharmacist, healthcare provider, or administrator, though such is not required. The unique identifier may be provided only upon the provision, storage, and verification of certain identification information. A patient user may be required to provide one or more forms of identification. Such identification may comprise, for example without limitation, a photo identification, a government issued driving license, a government issued passport, a credit card, a utility bill, some combination thereof, or the like. Upon provision of such information, the patient user may be issued a unique patient identifier. Entry of the unique patient identifier, for example at the patient system 18, may grant the patient read-only access to certain information stored at the patient prescription database 12 and associated with the entered unique patient identifier. Such information may comprise the list of prescriptions associated with the unique patient identifier. In this way, the user may be able to retrieve and view prescriptions available.

New pharmacy users may be required to provide one or more licenses or certifications such as, but not limited to, DEA certificates or equivalent government licensure for the geographic region the pharmacy operates in. Other certifications, licensures, or the like associated with the pharmacist's licensure to dispense certain medications may be provided. The pharmacist associated with a unique pharmacist identifier may be held responsible for any and all medications dispensed under the unique pharmacist identifier.

New healthcare provider users may be may be required to provide one or more licenses or certifications such as, but not limited to, medical licenses or equivalent government licensure for the geographic region the medical professional operates in. Other certifications, licensures, or the like associated with the healthcare provider's licensure to prescribe certain medications may be provided. The healthcare provider associated with a unique healthcare provider identifier may be held responsible for any and all medications dispensed under the unique healthcare provider identifier.

New administrator users may be required to provide one or more certifications for access. The administrator associated with a unique administrator identifier may be held responsible for any and all changes made under the unique administrator identifier.

The patient prescription database 12 may be configured to receive a unique identifier and check for the presence or non-presence of such a unique identifier at the patient prescription database 12. Unique identifier associated with a patient user may be granted read-only privilege as to prescriptions associated with an entered unique patient identifier. Unique identifiers associated with a pharmacy user may be granted write-privileges as related to the dispensing of medications. Unique identifier associated with a healthcare provider may be granted write-privileges as related to the generation of prescriptions. The patient prescription database 12 may further comprise a list of active users, who may be associated with users who have paid a service fee. When a service fee goes unpaid, the associated unique identifier may be removed from the list, or other action may be taken such that the user may no longer be able to access the patient prescription database 12.

Such service fees may be received by way of a payment module 26, though such is not required. The payment module 26 may be configured to receive payment information indicating the receipt of service fees. Such payment may be processed by way of credit card transactions, debit card transactions, bank transfers, electronic checks, some combination thereof, or the like.

The unique identifiers shown and/or described herein may comprise, for example without limitation, codes, alphanumeric identification, user id, passwords, digital certificates, facial recognition data, finger print data, or other biometric information, one-time access codes, some combination thereof, or the like. Each unique identifier may indicate one or more points of information about the underlying patient, prescription, healthcare provider, pharmacist, and/or administrator. For example, without limitation, a digit in the unique identifier may correspond with a particular geographic limitation. Another digit may correspond with a class of drug. These are merely exemplary and are not intended to be limiting.

The prescriptions and/or data related to the same (e.g., images thereof, e-prescription data, certifications, some combination thereof, or the like), which may be generally referred to herein as prescription(s), may reside within the patient prescription database 12. The patient prescription database 12 may be the only database that the prescriptions reside on during their existence, though such is not required. The patient prescription database 12 may be electronically partitioned so as to provide a private, virtual storage vault for the patient's prescription. For example, each patient's prescription(s) may be contained with a partitioned area of the patient prescription database 12 such that the area is not shared with any other patients. In exemplary embodiments, the prescribing healthcare provider may upload a prescription directly to the patient's partitioned area within the database 12 and the prescription may be removed once dispensed or expired. The data residing within a given one of the partitioned areas, in exemplary embodiments, may only be viewed and/or modified upon dual verification such as, but not limited to, by way of entry and verification of a unique patient identifier and one or more of: a unique healthcare provider identifier, a unique pharmacist identifier, and a unique administrator identifier.

Figure 5:
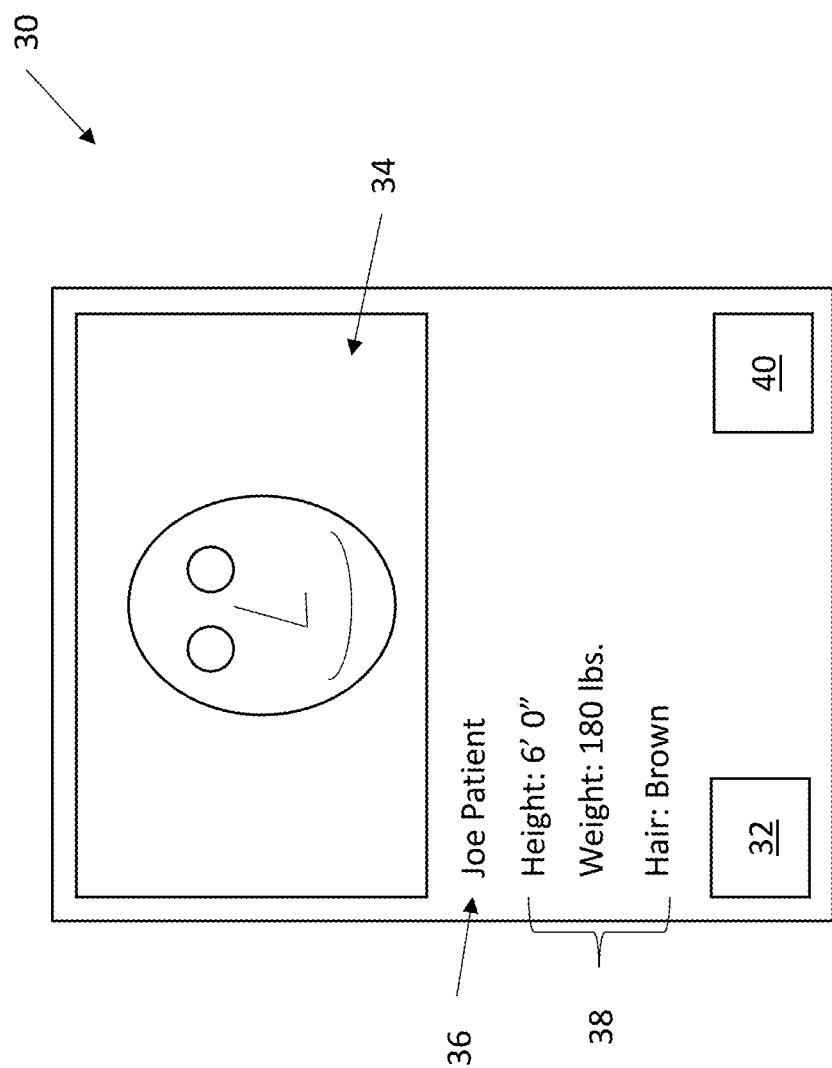
FIG. 5 is an exemplary identification device.

FIG. 5 is an exemplary identification device 30. In exemplary embodiments, the identification information described herein may take the form of an identification device 30 issued to the patient after enrollment. The identification device 30 may comprise a chip 32, magnetic strip, some combination thereof, or the like comprising the unique patient identifier and various unique prescription identifiers associated with the patient. Electronic copies of various identification documents may be stored at the chip 32 for manual comparison to presented documents. An identification device 30 may be issued to patient after successful enrolment.

The identification device 30 may be presented to the pharmacist for reading at the pharmacy system 16. Such reading may be performed at the one or more peripheral devices 22 though such is not required. Alternatively, or additionally, the identification device 30 may be presented at the patient system 18 for retrieving information associated with the unique patient identifier and/or the unique prescription identifiers. Such presentation may be made by way of an associated peripheral device 22, though such is not required. The identification device 30 may comprise additional identification information such as, but not limited to, a photo 34, identification information 36 (for example, without limitation, a name, social security number, ID number, some combination thereof, or the like), physical description information 38 (for example, without limitation, height, weight, hair color, eye color, some combination thereof, or the like), security devices 40 (for example, without limitation, watermark, hologram, some combination thereof, or the like), some combination thereof, or the like.

In exemplary embodiments, the same or similar identification device 30 may be provided to each pharmacist and/or healthcare provider following successful enrollment. The identification device 30 may comprise identification information and unique identifiers specific to the pharmacist and/or healthcare provider. The identification devices 30 may be presented to the pharmacist systems 16 and/or the healthcare provider systems 20. Such presentation may be made by way of peripheral devices 22, though such is not required.

Figure 6:
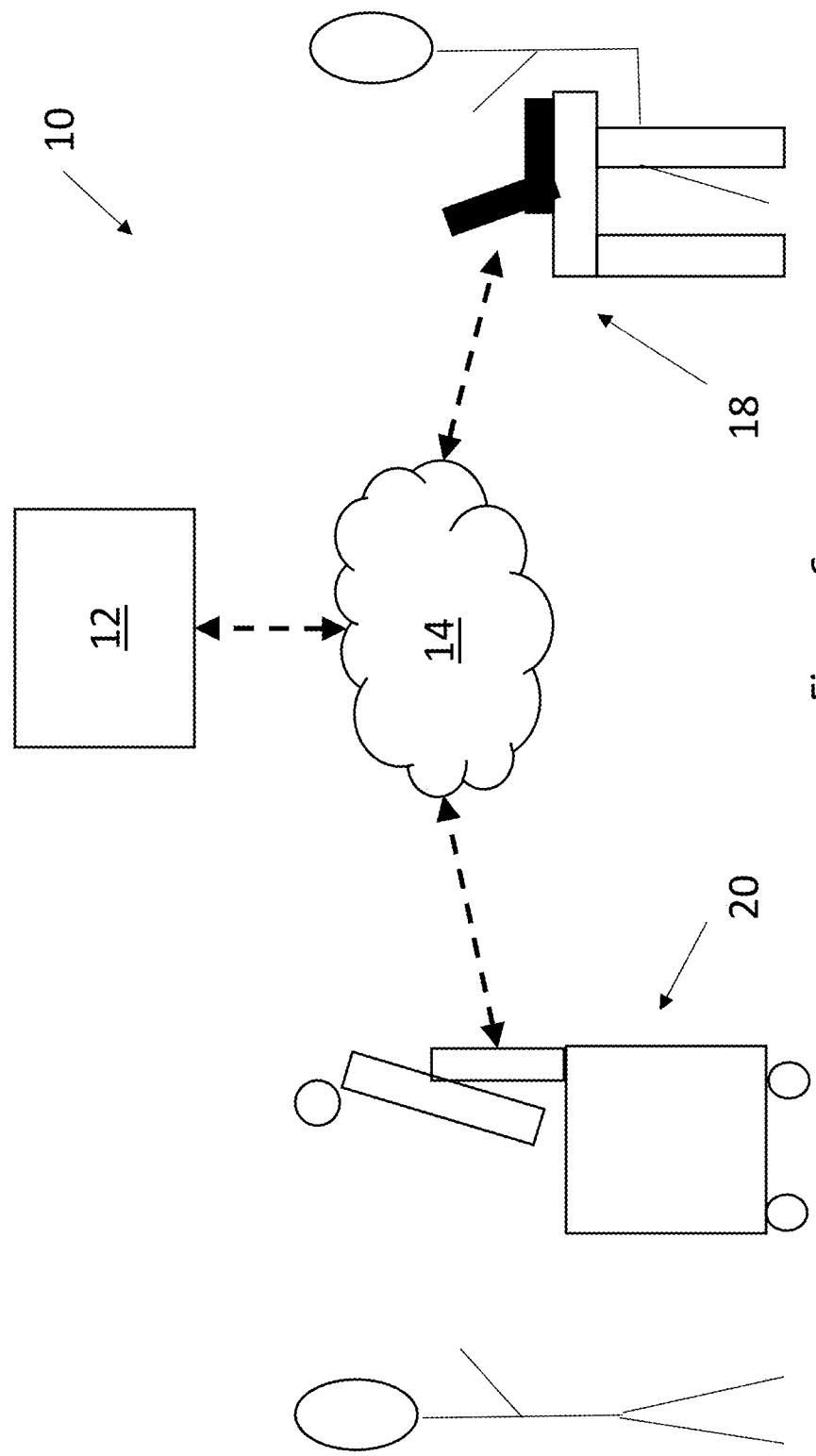
FIG. 6 is a plan view of an exemplary telehealth embodiment for use with the systems and methods of FIGS. 1-5.

FIG. 6 illustrates an exemplary telehealth embodiment of the system 10. The healthcare provider system 20 may comprise certain telehealth features, subsystems, and/or components such as, but not limited to, telephones, text messaging systems, email systems, VOIP systems, web cams, cameras, video conferencing systems, microphones, speakers, electronic displays, computers, tablets, smartphones, some combination thereof, or the like. The patient system 18 may comprise certain telehealth features, subsystems and/or components such as, but not limited to, telephones, text messaging systems, email systems, VOIP systems, web cams, cameras, video conferencing systems, microphones, speakers, electronic displays, computers, tablets, smartphones, some combination thereof, or the like. Electronic communication may be established between the patient and the healthcare provider by way of one or more networks 14.

The telehealth consultation may be arranged and/or provided by way of the telehealth module 42, though such is not required. The telehealth consultation may comprise audio and/or video components. The telehealth consultation may result in the prescription of one or more medications by way of a new prescription, a refill, some combination thereof, or the like.

Before, during, or after the telehealth consultation, evidence may be presented to and/or gathered by the healthcare provider. In exemplary embodiments, the evidence may comprise one or more images, videos, or the like of an injury or other condition. Alternatively, or additionally, the evidence may comprise test results, medical imaging results, self-reported symptoms, some combination thereof, or the like. The evidence may be related to the symptoms, diseases, conditions, or the like related to the prescription of medications.

The evidence may be uploaded to the patient prescription database 12 as described herein. In exemplary embodiments, the evidence may be uploaded to the same electronically partitioned area as the associate prescription(s). The evidence may remain in the electronically partitioned area for the same time as the associate prescription(s), though such is not required. For example, without limitation, the evidence may remain in the patient prescription database 12 for a longer period of time or indefinitely.

Before or after upload, the evidence may be associated with one or more prescriptions prescribed, refilled, or the like by the healthcare provider in conjunction with the consultation. The evidence may be retrieved from the patient prescription database 12 in conjunction with the retrieval of prescriptions as detailed herein.

The evidence may be retrieved when the prescription is accessed to verify the patient's identity. Alternatively, or additionally, the evidence may be accessed to compare a patient's current presentation with a former presentation for purposes of evaluating the adequacy of a prescription, the potential for fraud, mistake, and/or misunderstanding, the need for a refill, the need for further treatment, some combination thereof, or the like.

For example, without limitation, the patient may present with an ongoing skin condition. A picture of the skin condition may be uploaded as evidence with the prescription. The dispensing pharmacy may access the evidence to verify that the person to whom the pharmacy is dispensing the medication is indeed the patient. Alternatively, or additionally, the healthcare provider may access the evidence to compare the evidence against the patient's current symptoms to see if a refill, a different dose, an alternative medication, or the like are warranted. Alternatively, or additionally, the healthcare provider or another party may access the evidence to verify cause for prescribing and dispensing the medication.

As another example, without limitation, if the evidence associated with a narcotics prescription shows significant bruising around the midsection, but the party asserting themselves to be the patient for dispensation of the medication shows no such bruising a determination may be made that the prescription was obtained fraudulently, is no longer needed, some combination thereof, or the like. As another example, again without limitation, evidence of the same injury may be provided for multiple prescription for narcotics from multiple healthcare providers, tending to indicate fraud. Upon review of such multiple prescriptions for narcotics for the same injury, the healthcare provider and/or the pharmacist may determine that fraud may be occurring.

The patient prescription database 12 may be contained within a single electronic storage device or spread across multiple, locally or remotely located electronic storage devices.

Figure 7:
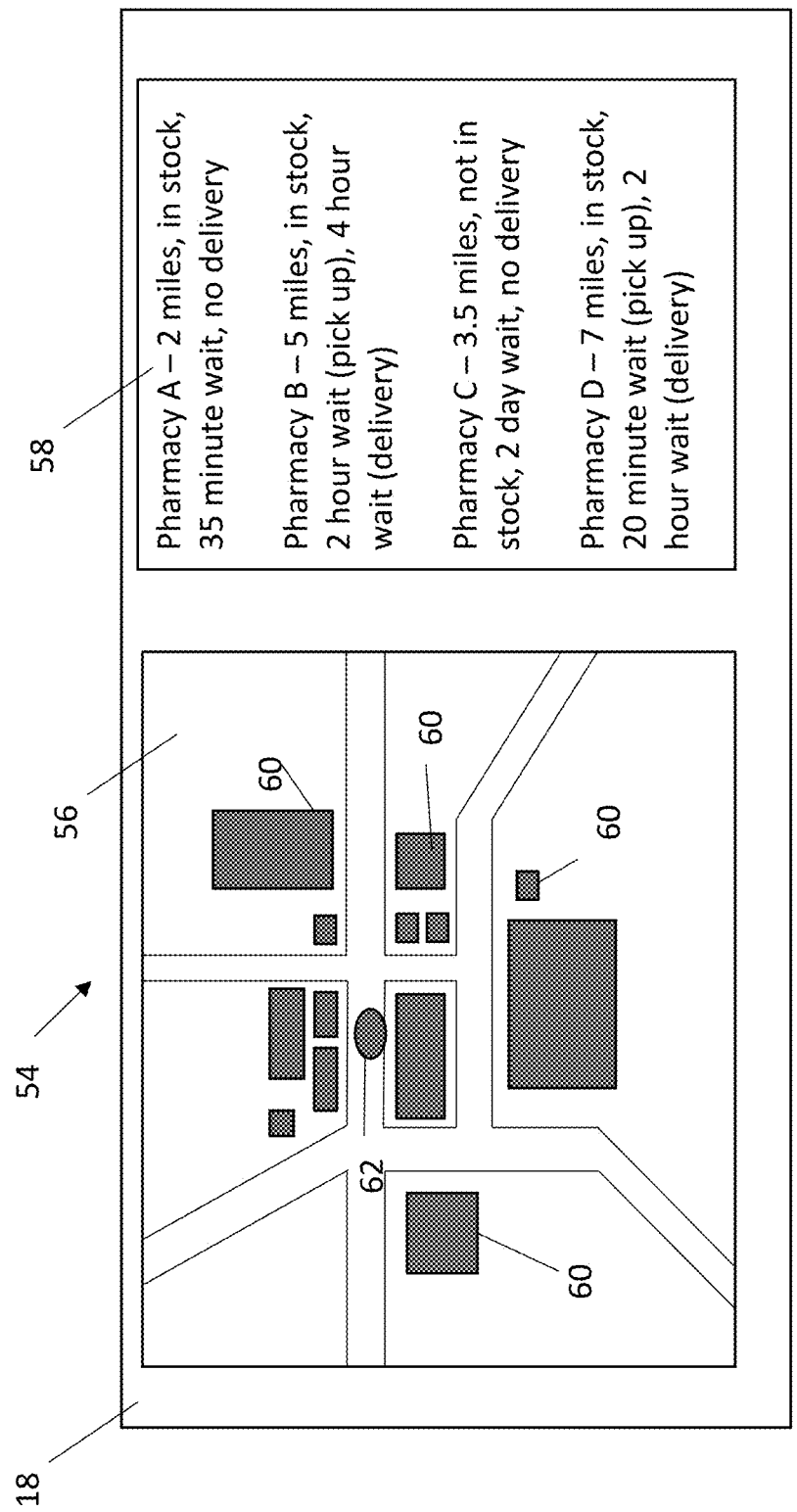
FIG. 7 is an exemplary pharmacy selection user interface for use with the systems and methods of FIGS. 1-6.

FIG. 7 is an exemplary user interface 54 for selecting a dispensing pharmacy 60. Pharmacies 60 associated with pharmacy systems 16 in communication with the patient prescription database 12 may be identified. In exemplary embodiments, pharmacies 60 within a predetermined or variable geographic distance from a location 62 of the patient system 18 and or another location 62 specified at the patient system 18 may be identified. Such pharmacies 60 may be shown on a map 56 in their approximate geographic location. The location 62 may also be shown on the map 56. The location may be determined by a location device at the patient system 18, manual entry, preprogramming, some combination thereof, or the like.

A listing of the pharmacies 60 may be generated at the same or a different screen 58. The listing may identify each of the pharmacies 60, their approximate geographic distance from the location 62, the availability of one or more prescriptions associated with the patient, and the approximate wait time for pick up and/or delivery (if available). The location of the pharmacy 60, and therefore the distance from the location specified by the patient system 18, may be determined by determined by a location device at the pharmacy system 16, manual entry, preprogramming, some combination thereof, or the like. In exemplary embodiments, the time for a prescription to be filled and/or delivered may be determined, at least in part, by the systems shown and described in U.S. Pat. No. 9,659,269 issued May 23, 2017, the disclosures of which are hereby incorporated by reference as if fully restated herein.

Figure 9:
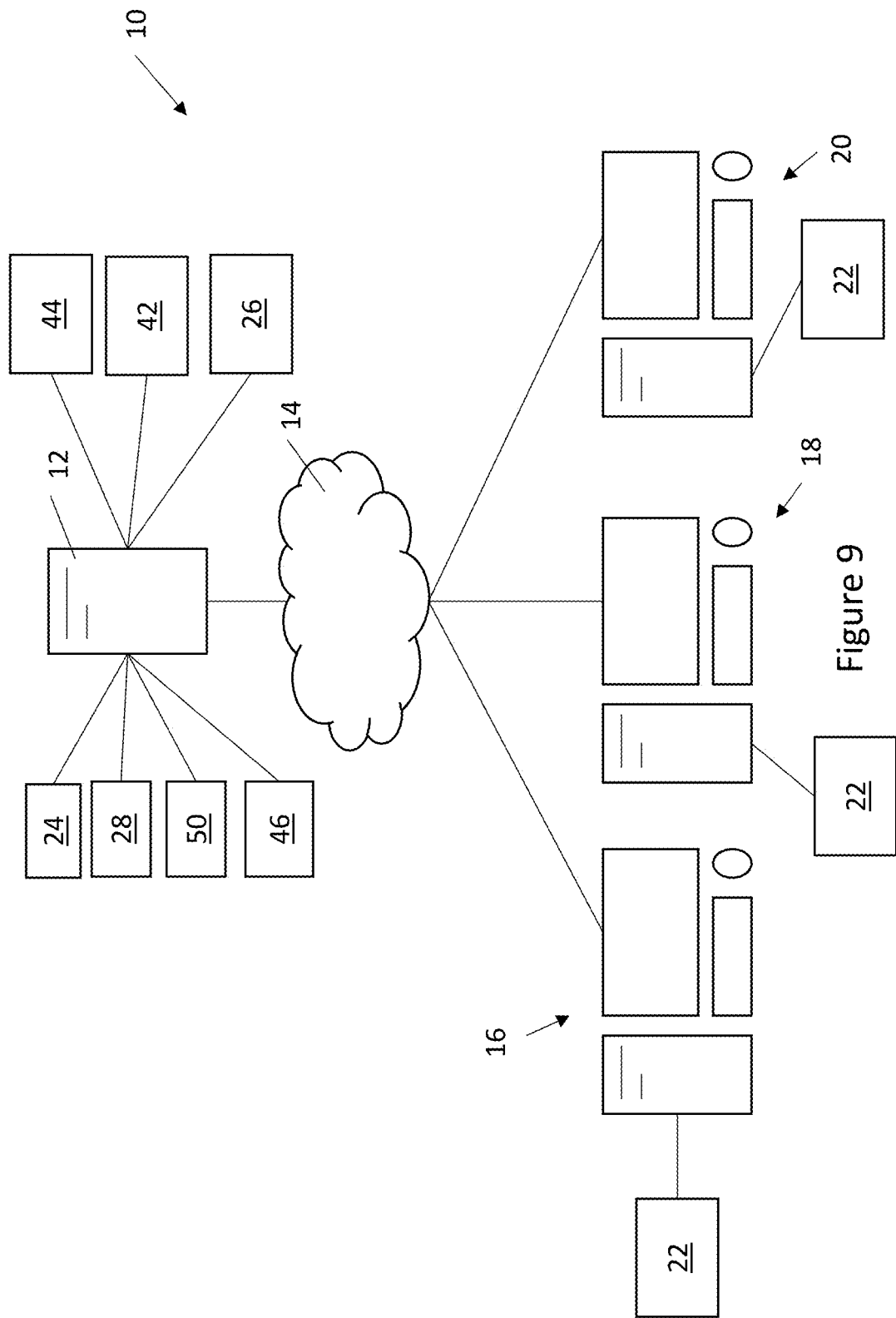
FIG. 9 is a plan view of another exemplary system.
Figure 10:
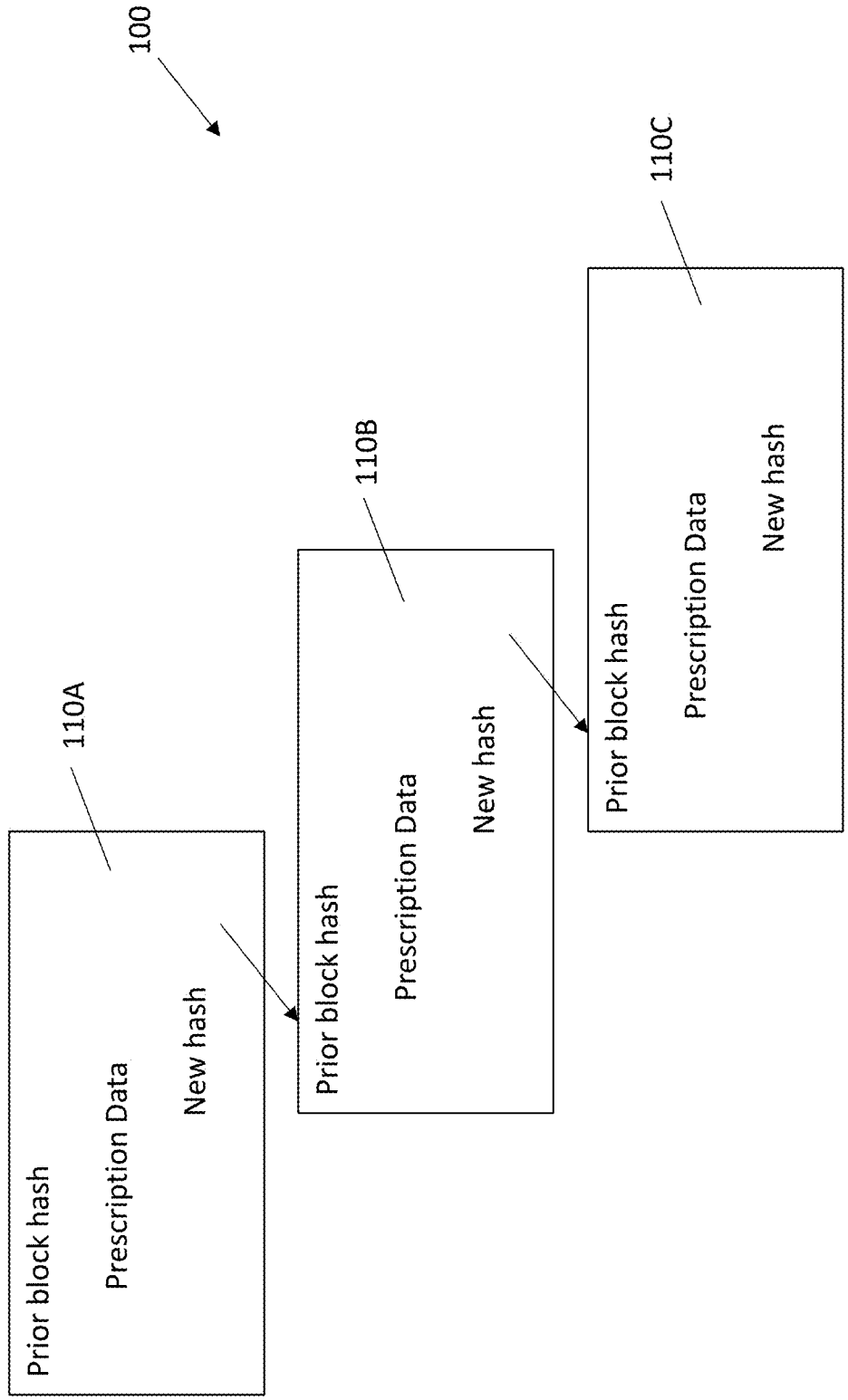
FIG. 10 is a simplified block diagram illustrating an exemplary blockchain for use with the systems and methods of FIGS. 1-9.
Figure 11:
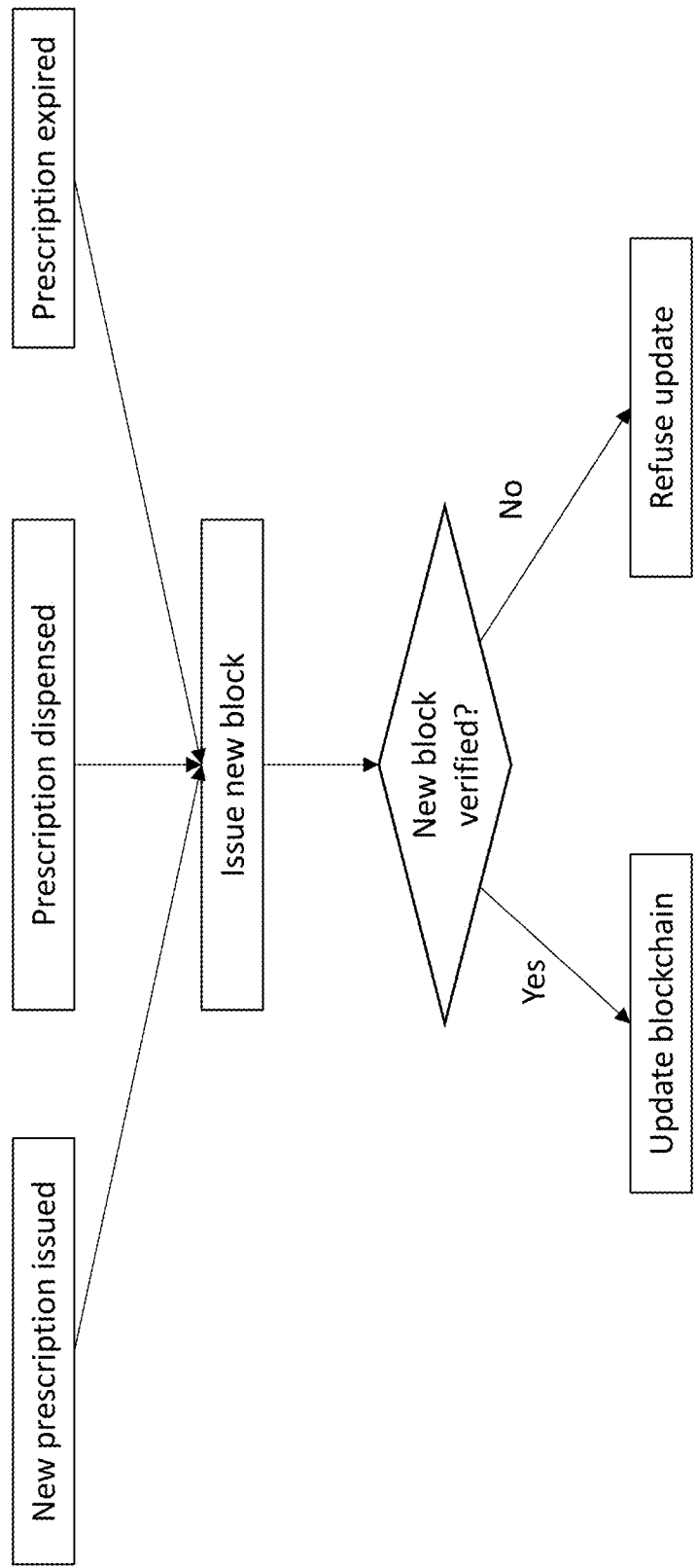
FIG. 11 is a flow chart with exemplary logic for operating the systems of FIGS. 1-10.

FIG. 9 through FIG. 11 illustrate another exemplary system 10 for use with one or more blockchains 100. One or more such blockchains 100 may be stored at the prescription database 12. The blockchain(s) 100 may be updated or otherwise managed by a blockchain module 50, such as in an automated fashion. The blockchain(s) 100 may store information regarding prescribed medications. For example, without limitation, such information may include medication(s) prescribed, amount prescribed, number of refills available, number of refills used, refill expiration date, dispensation information, patient information, dispensing pharmacy or pharmacist information, prescriber information, combinations thereof, or the like. Any type or kind of data shown and/or described herein may be stored at the blockchain(s) 100. The blockchain(s) 100 may be updated, such as by the issuance of new blocks 110A, 110B, 110C, with each medication prescribed, dispensed, and/or rendered expired to name some non-limiting examples. Each newly issued block 110A, 110B, 110C may comprise a hash of a prior issued block 110A, 110B, 110C, updates to the prescription information, and/or a new hash for example, without limitation.

The blockchain module 50 and/or the prescription database 12 may be configured to make the blockchain(s) 100 available to some or all of the users of the prescription database 12, such as in a read-only format. Such users may include, for example without limitation, the pharmacy systems 16, the patient systems 18, and/or the healthcare provider systems 20. Each of these user systems 16, 18, 20 may be configured to maintain a copy of the blockchain(s) 100. Updates, such as issuance of new ones of the blocks 100A, 100B, 100C made by the blockchain module 50 and/or the user systems 16, 18, 20. Such updates may be automatically disbursed to the blockchain module 50 and/or the user systems 16, 18, 20 for verification in exemplary embodiments. Once at least a majority of the user systems 16, 18, 20 and/or blockchain module 50 verify the update, such as the authenticity of the new block 100A, 100B, 100C, all user systems 16, 18, 20 and/or the blockchain module 50 may accept the change, and the blockchain 100 may be so updated, such as at the prescription database 12. In other exemplary embodiments, the blockchain module 50 may solely authenticate new blocks 100A, 100B, 100C and/or may have overriding control.

The user systems 16, 18, 20 may be configured to issue new blocks 100A, 100B, 100C and/or update the blockchain(s) 100 in an exemplary embodiment. For example, without limitation, at least certain ones of the user systems 16, 18, 20 may be configured to issue new blocks 100A, 100B, 100C in accordance with their write-access shown and/or described herein. In this manner, by way of non-limiting example, the pharmacy systems 16 may be configured to issue new blocks 100A, 100B, 100C as prescriptions are dispensed, the patient systems 18 may be configured to issue new blocks 100A, 100B, 100C requesting dispensation of prescriptions, and/or the healthcare provider systems 20 may be configured to issue new blocks 100A, 100B, 100C for new prescriptions. At least some of the user systems 16, 18, 20 may be configured to view the blockchain(s) 100 on an on-demand basis. In this manner, the user systems 16, 18, 20 may be able to verify updates to the blockchain(s) 100 and may be able to view their prescription information stored therein on an on-demand basis. In other exemplary embodiments, the blockchain module 50 may be configured to maintain overriding control of the blockchain(s) 100.

The blockchain module 50 may be configured to automatically delete blocks 100A, 100B, 100C related to expired prescriptions, removed user identifiers (such as shown and/or described herein), exhausted prescriptions (e.g., no refills left), and/or issue new blocks 100A, 100B, 100C indicating such expiration. In this manner, valuable electronic storage resources of the prescription database 12 may be maximized and/or verification work for the blockchain(s) 100 may be minimized.

In exemplary embodiments, a separate blockchain 100 may be generated for each prescribed medication. The blockchains 100 may be only readable by user systems 16, 18, 20 associated with the prescription and may be verifiable by the same. In this manner, access to such information may be controlled and permission limited. This may also minimize the burden of verifying new blocks 100A, 100B, 100C issued, such as by restricting verification to only the related ones of the user systems 16, 18, 20. Related ones of the user systems 16, 18, 20 may include, for example without limitation, the patient system 18 of the patient to whom the prescription is prescribed, any pharmacy systems 16 associated with dispensing of the medication prescribed, and the healthcare provider system 20 of the prescribing healthcare provider.

Payment for dispensed ones of said prescribed medications may be made by one or more cryptocurrencies. Such cryptocurrency payment may be managed by way of the payment module 26 and/or the blockchain module 50. For example, without limitation, invoices may be generated by the payment module 26 for transmission to the customer and payment information may be received through the payment module 26. Where such payment is desired in cryptocurrency, the payment module 26 may be configured to obtain current exchange rates for such cryptocurrencies based on third-party information available over the internet. The payment module 26 may be configured to obtain the payment and electronically exchange it for a desired currency (e.g., USD). The blockchain module 50 may be configured to update or issue a new block 110A, 110B, 110C indicating the payment and exchange. The payment module 26 and/or blockchain module 50 may be configured to utilize the same or similar processes for converting payment from a denomination specific to a country of dispensation, for example, to another desired currency (e.g., pesos to USD). In this manner, payment may be facilitated in a global economy.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing devices. The electronic devices may be personal computers, smartphone, tablets, databases, servers, or the like. The electronic connections described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. A system for providing world-wide access to prescribed medications comprising:
    a prescription database comprising:
        unique patient identifiers;
        prescriptions, each associated with one of the unique patient identifiers;
        unique pharmacist identifiers;
        patient authentication information, each associated with one of the unique patient identifiers; and
        one or more blockchains comprising one or more of said unique patient identifiers, said prescriptions, said unique pharmacist identifiers, and said patient authentication information;
    pharmacy systems in electronic communication with the prescription database;
    one or more non-transitory electronic storage devices associated with the prescription database and comprising software instructions, which when executed, configure one or more processors to:
        receive a unique patient identifier from a particular one of the pharmacy systems;
        receive entered patient authentication information from the particular pharmacy system;
        verify that the entered patient authentication information matches stored patient authentication information associated with the received unique patient identifier;
        receive a unique pharmacist identifier from the particular pharmacy system;
        verify that the received unique pharmacist identifier matches one of the unique pharmacist identifiers stored at the prescription database;
        display, at the particular pharmacy system, each of the prescriptions associated with the received unique patient identifier;
        receive a user selection of one or more of the displayed prescriptions from the particular pharmacy system;
        receive, from the particular pharmacy system, dispensation information comprising an amount of medication dispensed, a time and date of dispensation, and a reason for dispensation; and update, at the prescription database, the user selected prescriptions with the dispensation information by issuing one or more new blocks to the one or more blockchains comprising a hash of a prior block, the dispensation information, and a new hash.

2. The system of claim 1 further comprising:
patient systems, wherein the one or more non-transitory electronic storage devices comprise additional software instructions, which when executed, configure the one or more processors to:
transmit each of said one or more new blocks to each of the pharmacy systems and each of the patient systems for verification; and
update said one or more blockchains with said one or more new blocks upon receipt of data indicating that at least half of said number of pharmacy systems and said patient systems accept said one or more new blocks.

3. The system of claim 2 further comprising:
the one or more non-transitory electronic storage devices comprise additional software instructions, which when executed, configure the one or more processors to make said one or more blockchains available to each of said pharmacy system and each of said patient systems on an on-demand basis.

4. The system of claim 1 further comprising:
patient systems, each associated with one of the unique patient identifiers;
the one or more non-transitory electronic storage devices comprise additional software instructions, which when executed, configure the one or more processors to:
transmit each of said one or more new blocks to each of the particular pharmacy system and a particular one of the patient systems associated with the received one of the unique patient identifiers for verification; and
update said one or more blockchains with said one or more new blocks upon receipt of data indicating that said particular pharmacy system and said particular one of said patient systems accept said one or more new blocks.

5. The system of claim 4 wherein:
each of said one or more blockchains are specific to one or said prescriptions; and
the one or more non-transitory electronic storage devices comprise additional software instructions, which when executed, configure the one or more processors to make individual ones of said one or more blockchains available to individual ones of said pharmacy systems and individual ones of said patient systems on an on-demand basis specific to the individual ones of said prescriptions associated with the individual ones of the pharmacy systems and the individual ones of the patient systems.

6. The system of claim 1 wherein:
each of said prescriptions is associated with an expiration date; and
said one or more non-transitory electronic storage devices comprise additional software instructions, which when executed, configure the one or more processors to:
determine a current date; and
remove blocks of said one or more blockchains associated with an expiration date prior to the current date.

7. The system of claim 6 further comprising:
the one or more non-transitory electronic storage devices comprise additional software instructions, which when executed, configure the one or more processors to:
automatically associate a default expiration date with each of said one or more prescriptions;
said prescription information comprises a class of drug; and
said default expiration data is specific to the class of drug.

8. The system of claim 1 wherein:
each of said one or more prescriptions is associated with a maximum number of refills; and
said one or more non-transitory electronic storage devices comprises additional software instructions, which when executed, configure the one or more processors to:
determine a number of times a prescription has been refilled; and
remove blocks of said one or more blockchains associated with a number of refills exceeding the maximum number of refills.

9. The system of claim 8 wherein:
said one or more non-transitory electronic storage devices comprises additional software instructions, which when executed, configure the one or more processors to automatically associate a default maximum number of refills with each of said one or more prescriptions, wherein said prescription information comprises a class of drug, and wherein said default maximum number of refills is specific to the class of drug.

10. The system of claim 1 wherein:
each of the unique pharmacist identifiers is associated with one of a number of geographic areas, and each of the number of geographic areas are associated with one or more languages;
said system further comprises a translation module in electronic communication with the prescription database configured to provide machine translations between each of the one or more languages;
said one or more non-transitory electronic storage devices comprise additional software instructions, which when executed, configure the one or more processors to:
determine the geographic area associated with the received unique pharmacist identifier;
determine a language associated with the determined geographic area;
display, at the particular one of the number of pharmacy systems, each of the one or more prescriptions associated with the received unique patient identifier in the determined language;
said prescription database comprises medication brand names for each medication such as that at least some of the medications are associated with more than one of the medication brand names, wherein each of the medication brand names for each of the medications is associated with one of the number of geographic areas and one or more prescriptions;
said one or more non-transitory electronic storage devices comprise additional software instructions, which when executed, configure the one or more processors to, for each retrieved prescription, retrieve a particular one of the medication brand name associated with the determined geographic area and the retrieved prescription for a particular one of the medication so that the medication brand name specific to the determined geographic area and the particular one of the medications is displayed;
said medication brand names comprise generic medication names, each associated with one of the medications and one or more geographic areas; and said one or more non-transitory electronic storage devices comprise additional software instructions, which when executed, configure the one or more processors to, for each retrieved prescription, retrieve the generic medication name associated with the determined geographic area and the particular medication.

11. The system of claim 1 further comprising:
a payment module in electronic communication with the prescription database and configured to receive payment information in a number of different currency forms, wherein said one or more non-transitory electronic storage devices comprise additional software instructions, which when executed, configure the one or more processors to execute an electronic transaction based on said payment information, wherein said electronic transaction includes an electronic exchange of currency provided in a given denomination in said payment information into a desired denomination where said given denomination is different from said desired denomination.

12. The system of claim 1 further comprising:
patient systems, each in electronic communication with the prescription database;
healthcare provider systems, each in electronic communication with the prescription database; and
unique healthcare provider identifiers stored at the prescription database, wherein each unique healthcare provider identifier is associated with one or more certification or licensure documents, wherein each unique healthcare provider identifier is associated with one or more unique patient identifiers;
wherein the one or more non-transitory electronic storage devices comprise additional software instructions, which when executed, configure the one or more processors to:
provide read-only access at a particular one of the patient systems which has transmitted a unique patient identifier matching one of the unique patient identifiers in the unique patient identifiers stored at the prescription database limited to blocks of the one or more blockchains associated with the received unique patient identifier;
provide ability to generate new blocks with the dispensation information upon receipt of a unique pharmacist identifier matching a unique pharmacist identifier stored at the prescription database limited to dispensation information for new blocks associated with certain of the one or more prescriptions associated with the received unique patient identifier;
provide ability to generate new blocks for new ones of said prescriptions at a particular one of the healthcare provider systems which has transmitted a unique healthcare provider identifier matching one of the unique healthcare provider identifiers in the unique healthcare provider identifiers stored at the prescription database.

13. The system of claim 1 wherein:
each of the unique patient identifiers comprise a user id and password; and
each of the unique pharmacist identifiers comprise a user id and password.

14. The system of claim 1 wherein:
said patient authentication information comprises any one or more of: a code, password, and biometric information.

15. A method for providing world-wide access to prescribed medications, said method comprising the steps of:
receiving a unique patient identifier from a particular one of multiple pharmacy systems;
receiving entered patient authentication information from the particular one of the multiple pharmacy systems;
verifying that the entered patient authentication information matches patient authentication information stored at a prescription database associated with the received unique patient identifier, wherein said prescription database comprises the unique patient identifiers, each associated with certain of the patient authentication information;
receiving a unique pharmacist identifier from the particular one of the multiple pharmacy systems;
verifying that the received unique pharmacist identifier matches one of multiple unique pharmacist identifiers stored at the prescription database;
displaying, at the particular one of the pharmacy systems, each prescription stored at the prescription database in association with the received unique patient identifier, wherein said prescription database comprises multiple prescriptions, each associated with one of the unique patient identifiers;
receiving a user selection of one or more of the displayed prescriptions from the particular one of the pharmacy systems;
receiving, from the particular one of the pharmacy systems, dispensation information comprising an amount of medication dispensed, a time and date of dispensation, and a reason for dispensation; and
generating, for storage at the prescription database, one or more blocks for one or more blockchains stored at the prescription database comprising data regarding a hash of an existing block in said one or more blockchains, the user selected prescriptions, the dispensation information, and a new hash.

16. The method of claim 15 further comprising the steps of:
transmitting said one or more blocks to at least the particular one of the pharmacy systems;
receiving, from the at least the particular one of the pharmacy systems indication that said one or more blocks are authentic; and
updating said one or more blockchains with said one or more blocks.

17. The method of claim 15 further comprising the steps of:
receiving a request from a particular one of multiple patient systems to view prescriptions, wherein said request comprises one of said unique patient identifiers;
querying said prescription database for blocks associated with said one or more blockchains regarding certain of said prescriptions associated with said received unique patient identifiers; and
transmitting copies of said blocks associated with said one or more blockchains regarding said certain of said prescriptions associated with said received unique patient identifier to said particular one of said patient systems for read-only access.

18. The method of claim 15 wherein:
each of said one or more blockchains is specific to a given one of said one or more prescriptions.

19. The method of claim 15 wherein:
each of said one or more blockchains is specific to a given one of said unique patient identifiers.

20. The method of claim 15 further comprising the steps of:

querying said prescription database for any of said prescriptions associated with an expiration date prior to a current data;

removing blocks of said one or more blockchains associated with any of said prescriptions associated with an expiration date prior to a current date;

querying said prescription database for any of said prescriptions associated with said dispensation information indicating a number of refills meeting or exceeding a maximum number of refills; and removing blocks of said one or more blockchains associated with any of said prescriptions associated with said dispensation information indicating a number of refills meeting or exceeding a maximum number of refills.

21. The method of claim 15 wherein:

wherein said patient authentication information comprises any one or more of: a code, password, and biometric information.

22. A system for providing world-wide access to prescribed medications comprising:

a centralized prescription database comprising:

a number of blockchains, each comprising:

one of multiple unique patient identifiers, wherein each of said unique patient identifiers is associated with one of multiple patients;

one or more of multiple prescriptions for the one of the unique patient identifiers; and one or more of multiple unique pharmacist identifiers;

patient authentication information associated with each of the unique patient identifiers, wherein said patient authentication information comprises any one or more of: a code, password, and biometric information;

pharmacy certification information associated with each of the unique pharmacist identifiers; and multiple pharmacy systems, each in electronic communication with the centralized prescription database;

multiple patient systems, each in electronic communication with the centralized prescription database;

one or more non-transitory electronic storage devices associated with said centralized prescription database and comprising software instructions, which when executed, configures one or more processors to:

receive a unique patient identifier from a particular one of the pharmacy systems;

receive entered patient authentication information from the particular one of the pharmacy systems;

verify that the entered patient authentication information matches stored patient authentication information associated with the received unique patient identifier;

receive a unique pharmacist identifier from the particular one of the pharmacy systems;

verify that the received unique pharmacist identifier matches one of the unique pharmacist identifiers stored at the centralized prescription database;

display, at the particular one of the pharmacy systems, each of the one or more prescriptions associated with the received unique patient identifier;

receive a user selection of one or more of the displayed prescriptions from the particular one of the pharmacy systems;

receive, from the particular one of the pharmacy systems, dispensation information comprising an amount of medication dispensed, a time and date of dispensation, and a reason for dispensation;

update, at the prescription database, a respective one of the blockchains associated with the user selected prescriptions with the dispensation information by issuing one or more new blocks to the respective one of the blockchains comprising a hash of a prior block, the dispensation information, and a new hash;

receive a request from a particular one of the patient systems for prescription information comprising one of the unique patient identifiers;

query said prescription database to retrieve each of said blockchains associated with said particular one of said number of unique patient identifiers; and transmit each of said retrieved ones of said number of blockchains to said particular one of said number of patient systems for display.

* * * * *